United States Patent [19]

Malik et al.

[11] Patent Number: 5,683,725
[45] Date of Patent: Nov. 4, 1997

[54] MODULATION OF SUBSTANCE P BY COMPOUNDS CONTAINING CALCIUM SULFATE AND METHODS RELATING THERETO

[75] Inventors: Sohail Malik, Seattle; Rolland F. Hebert; Min Yee, both of Bellevue, all of Wash.

[73] Assignee: BioFrontiers, Inc., Bellevue, Wash.

[21] Appl. No.: 449,949

[22] Filed: May 25, 1995

[51] Int. Cl.$^6$ ............................ A61K 33/04; A61K 33/06
[52] U.S. Cl. ........................ 424/696; 424/682; 424/709
[58] Field of Search ............................... 424/696, 709, 424/682

[56] References Cited

U.S. PATENT DOCUMENTS

| | | | |
|---|---|---|---|
| 4,554,139 | 11/1985 | Worthington et al. | 423/166 |
| 4,689,223 | 8/1987 | Arias | 424/682 |
| 4,735,802 | 4/1988 | Le | 424/682 |
| 4,915,936 | 4/1990 | Patterson et al. | 424/49 |

FOREIGN PATENT DOCUMENTS

| | | |
|---|---|---|
| WO 88/09665 | 12/1988 | WIPO . |
| WO 94/09798 | 5/1994 | WIPO . |
| WO 95/05752 | 3/1995 | WIPO . |

OTHER PUBLICATIONS

Derwent Abstracts, Accession No. 96–246881 C25, 1996, Abstracting JP 8099848 (Apr. 16, 1996).
Bartold et al., "Substance P: An Immunohistochemical and Biochemical Study in Human Gingival Tissues. A Role for Neurogenic Inflammation?," *J. Periodontol* 65:1113–1121 (1994).
Györfi et al., "Role of substance P (SP) in development of symptoms of neurogenic inflammation in the oral mucosa of the rat," *J. Periodont Res* 28:191–196 (1993).
Joos et al., "Sensory neuropeptides and the human lower airways: present state and future directions," *Eur. Respir. J.* 7:1161–1171 (1994).
Sestini et al., "Ion Transport in Rat Tracheal Epithelium In Vitro. Role of Capsaicin–sensitive Nerves in Allergic Reactions," *AM Rev Respir* 141:393–397 (1990).
Nakai et al., "Substance P–induced cutaneous and bronchial reactions in children with bronchial asthma," *Ann. Allergy* 66:155–161 (1991).
Hagiwara et al., "Studies on Neurokinin Antagonists. 4. Synthesis and Structure–Activity Relationships of Novel Dipeptide Substance P Antagonists: $N^2$–[(4R)–4–Hydroxy–1–[(1–methyl–1H–indol–3–yl) carbonyl]– L–prolyl]–N–methyl–N–(phenylmethyl)– 3–(2–naphthyl)– L–alaninamide and Its Related Compounds." *J. Med. Chem.* 37:2090–2099 (1994).
Wallengren, J., "Substance P antagonist inhibits immediate and delayed type cutaneous hypersensitivity reactions," *Br. J Derm.* 124:324–328 (1991).
Felten et al., "Fundamental Aspects of Neural–Immune Signaling," *Psycother. Psychosom.* 60:46–56 (1993).

Lee et al., "Blockade by Oral or Parenteral RPR 100893 (a non–peptide $NK_1$ receptor antagonist) of neurogenic plasma protein extravasation within guinea–pig dura mater and conjunctiva," *Br. J. Pharmacol.* 112:920–924 (1994).
Liu et al., "The effects of capsaicin on pulpal blood flow," *Proc. Finn. Dent. Soc.* 88(Supp. I):463–467 (1992).
Nieber et al., "The Possible Role of Substance P in the Allergic Reaction, Based on Two Different Provocation Models," *Int. Arch. Allergy Appl. Immunol.* 94:334–338 (1991).
Okamoto et al., "Cytokine Expression After the Topical Administration of Substance P to Human Nasal Mucosa. The Role of Substance P in Nasal Allergy," *J. Immunol.* 151:4391–4398 (1993).
Rameshwar et al., "In Vitro Stimulatory Effect of Substance P on Hematopoiesis." *Blood* 81:391–398 (1993).
Alleva et al., "Capsaicin Affects Aggressive Behavior, But Not Hot Plate Responding, of Adult Male Mice," *Physiology & Behavior* 49:715–719 (1991).
Crimi et al., "Influence of antihistamine (astemizole) and anticholinergic drugs (ipratropium bromide) on bronchoconstriction induced by substance P," *Ann. Allergy* 65:115–120 (1990).
Elliot et al., "Modulation of the rat mesolimbic dopamine pathway by neurokinins," *Behavioural Brain Research* 51:77–82 (1992).
Evangelista et al., "Duodenal SP–like immunoreactivity is decreased in experimentally–induced duodenal ulcers," *Neuroscience Letters* 112:352–355 (1990).
Malek–Ahmadi, P., "Substance P and Neuropsychiatric Disorders: An Overview," *Neuroscience and Biobehavioral Reviews* 16:365–369 (1992).
Moore & Black, "Neuropeptides," *Neurosurg. Rev.* 14:97–110 (1991).
Moussaoui et al., "Inhibition of neurogenic inflammation in the meninges by a non–peptide $NK_1$ Receptor Antagonist, RP 67580," *Eur. J. Pharma.* 238:421–424 (1993).
Shuster, S., "Capsaicin and the cause of causalgia," *Lancet* 345:160–161 (1995).
Tsuji and Cook, "Origin of thromboxane–mediated constriction due to neuropeptides in canine basilar artery," *Eur. J Pharma.* 264:77–80 (1994).

(List continued on next page.)

*Primary Examiner*—John Pak
*Attorney, Agent, or Firm*—Seed and Berry LLP

[57] ABSTRACT

Modulation of substance P by compounds containing calcium sulfate is disclosed. Preferred calcium sulfate compounds include syngenite, görgeyite and gypsum. Methods of this invention include the modulation of substance P, as well as methods for preventing or treating conditions associated with substance P, by administering to an animal an effective amount of a calcium sulfate compound. Conditions associated with substance P include headaches and migraine, neurogenic inflammation, emesis, nausea and vomiting, cough and bronchitis, obesity, allergy, asthma, hemorrhoids and anal fissures, ulcer, fever, infertility and periodontal disease.

16 Claims, 4 Drawing Sheets

OTHER PUBLICATIONS

Dockray, G., "Substance P and Other Tachykinins," in *Gut Peptides: Biochemistry and Physiology*, Raven Press, New York, N.Y. 1994 (edited by John Walsh and Graham Dockray), pp. 401–422.

Dryden et al., "Neuropeptide Y and energy balance: one way ahead for the treatment of obesity?" *Eur. J Clin. Invest.* 24:293–308 (1994).

Paus et al., "Hair Growth Induction by Substance P," *Lab. Invest.* 71:134–140 (1994).

Talley et al., "GR 38032F (Ondansetron), A Selective $5HT_3$ Receptor Antagonist, Slows Colonic Transit in Healthy Man," *Digestive Diseases and Sciences* 35:477–480 (1990).

Karlberg, B., "Cough and inhibition of the renin–angiotensin system," *Journal of Hypertension* 11(supp.3):S49–S52 (1993).

Blatteis, "Role of the OVLT in the febrile response to circulating pyrogens," *Progress in Brain Research* 91:409–412 (1992).

Nadel, J., "Mechanisms of Inflammation and Potential Role in the Pathogenesis of Asthma," *Allergy Proc.* 12:85–88 (1991).

Williams et al., "Reduced Hypothalamic Neurotensin Concentrations in the Genetically Obese Diabetic (ob/ob) Mouse: Possible Relationship to Obesity," *Metabolism* 40:1112–1116 (1991).

Blatteis et al., "Neuromodulation of Fever. A Possible Role for Substance P," *Ann. N.Y. Acad. Sci.* 741:162–173 (1992).

Györfi et al., "Neurogenic inflammation and the oral mucosa," *J. Clin Periodontol* 19:731–736 (1992).

Ohkubo et al., "Role of Substance P in Neurogenic Inflammation in the Rat Incisor Pulp and the Lower Lip," *Archs oral Biol.* 38:151–158 (1993).

Schmid et al., "Temperature sensitivity of neurons in slices of the rat PO/AH area: effect of bombesin and substance P," *Am. J. Physiol.* 264:R449–R455 (1993).

Barnes, R., "Neurogenic Inflammation and Asthma," *Journal of Asthma* 29:165–180 (1992).

Mosimann et al., "Allergens, IgE, mediators, inflammatory mechanisms. Substance P, calcitonin gene-related peptide, and vasoactive intestinal peptide increase in nasal secretions after allergen challenge in atopic patients," *J Allergy Clin Immunol* 92:95–104 (1993).

Debeljuk and Bartke, "Immunoreactive Substance P and Neurokinin A in the Hypothalamus and Anterior Pituitary Gland of Siberian and Syrian Hamsters and of Rats," *J Reproduction and Fertility* 101:427–434 (1994).

Chiwakata et al., "Tachykinin (Substance-P) Gene Expression in Leydig Cells of the Human and Mouse Testis," *Endocrinology* 128:2441–2448 (1991).

Kerdelhué et al., "Hypothalamo–Anterior Pituitary Gonadotropin–Releasing Hormone and Substance–P Systems during the 17β–Estradiol–Induced Plasma Luteinizing Hormone Surge in the Ovariectomized Female Monkey," *Endocrinology* 132:1151–1157 (1993).

MODULATION OF SUBSTANCE P BY COMPOUNDS CONTAINING CALCIUM SULFATE AND METHODS RELATING THERETO

TECHNICAL FIELD

The present invention relates generally to a method of modulating substance P by compounds containing calcium sulfate, particularly syngenite, görgeyite and gypsum, and more specifically, to the synthesis of such compounds as well as their use to treat a variety of conditions associated with substance P.

BACKGROUND OF THE INVENTION

Substance P, along with neurokinin A and neurokinin B, are members of the tachykinin family of mammalian regulatory peptides (Dockray, *Gut Peptides: Biochemistry and Physiology,* Walsh and Dockray, editors, Raven Press, Ltd, New York, N.Y., pp. 401–422, 1994). In 1931, substance P was the first of the gut neuropeptides to be discovered (von Euler and Gaddum, *J. Physiol.* 72:74–87, 1931). Nearly 40 years later, substance P was isolated and sequenced from bovine hypothalamus, and determined to be an undecapeptide (Chang and Leeman, *J. Biol. Chem.* 245:4784–4790, 1970; Chang and Leeman, *Nature* 232:86–87, 1971). More recently, multiple receptor subtypes (i.e., NK1, NK2 and NK3) for the various tachykinin neuropeptides have been cloned and sequenced, with substance P being considered the natural ligand for receptors of the NK1 subtype (Dockray, pp. 408–409).

Substance P is stored in the secretory granules of substance P immunoreactive nerves, which are afferent, small diameter, unmyelinated polymodal, C-type fibers with dual functions. Upon orthodromic stimulation by noxious stimuli, substance P is released from the spinal tract for central transmission of nociceptive information. A secondary function involves release of substance P and other neuropeptides from collateral nerve terminals and peripheral tissue following antidromic noxious stimulation, resulting in "neurogenic inflammation." Such peripheral release of substance P has been implicated as a neurogenic promoter of various inflammatory processes, including asthma, rhinitis, conjunctivitis, and inflammation of the skin and mucosa (see Bartold et al., *J. Periodontol* 65:1113–21, 1994). Substance P has also been found to be a potent vasodilator and increases vascular permeability, and has pro-inflammatory effects on neutrophils, macrophages, mast cells, lymphocytes, and endothelial cells (Bartold et al.). In addition to the central and peripheral nervous system, substance P immunoreactive nerves, and thus substance P itself, have been found in a variety of different mammalian tissues, including smooth muscles of the arteries and veins, pulmonary, urinary and gastrointestinal tracts, basal ganglia, substantia nigra, striatonigral pathways, hypothalamus, retina, hair follicles, gingival tissues, prostate gland, and even in spermatozoa.

In short, distribution of substance P is nearly ubiquitous in mammalian tissues. This wide distribution is believed to be due, at least in part, to the association of substance P (either directly or indirectly) with numerous processes and/or conditions, including neurogenic inflammation (Barnes, *J. Asthma* 29:165–180, 1992; Ohkubo, *Archs. Oral Biol.* 38:151–158, 1993), pain (Chu, et el., *Annals of N.Y. Acad. Sci.* 632:488–489, 1991), allergy (Nieber et el., *Int Arch. Allergy Appl. Immunol.* 94:334–338, 1991), asthma (Nadel, *Allergy Proc.* 12(2):85–88, 1991; Nakai et al., *Ann. Allergy* 77:155–161, 1991; Joos et el., *Eur. Respir. J. Z:*11161–1171, 1994), cough (Yoshihara et al., *Regulatory Peptides* 46:238–40, 1993), emesis (Tattersall et el., *European J. Pharm.* 250:R5–R6, 1993; Knox et el., *Brain Res. Bulletin* 31:477–84, 1993), bronchoconstriction (Joos et al., *European Respir. J.* 7:1161–1171, 1994; Rechtman et al., *European J. Pharm.* 201:69–74, 1991), obesity (Baroncelli et al., *Functional Neurology* 4:183–34, 1989), fertility (Chiwakata et al., *Endocrinology* 128:2441–2448, 1991 ), Alzheimer's disease (Khalil et el., *Brain Research* 651:227–235, 1994), psychotic behavior (Elliot et al., *Neuropeptides* 19:119–126, 1991; Elliot et el., *Behav. Brain Res.* 51:77–82, 1992; Mousseau et al., *Metabolic Brain Disease* 9:249–255, 1994), headaches/migraine (Moussaoui et al., *European J. Pharmacol.* 238:421–424, 1993; Nakano et al., *Headache* Nov.–Dec., 1993; Edvinsion et al., *Cephalolgia* 14:320–327, 1994), and immune response (Covas, *Clin. and Exp. Immunology* 96:384–388, 1994). An overview of recent research directed to substance P and related peptides is presented in *Annals N.Y. Acad. Sciences,* Leeman, Krause and Lembeck editors, Vol. 632, pp. 1–497, 1991.

The role of substance P as a promoter of neurogenic inflammation associated with periodontal disease has received attention in recent years (Györfi et al., *J. Clin. Periodontology* 19:731–736, 1992). The term "periodontal disease" is generally used to describe disorders of the periodontium, ranging from the relatively benign form of gingivitis confined to the marginal tissues, to more aggressive forms such as rapidly progressive periodontitis, in which the disease process leads to loss of connective tissue attachment to the root surfaces, loss of alveolar support, and impaired function of the dentition (see generally Armitage, *Periodontology 2000* 7:39–53, 1995).

Gingivitis affects approximately 80% of all people in the United States by the age of 15. It is characterized by redness, gingival bleeding, swelling, gingival sensitivity and tenderness (Johnson et al., *J. Periodontol* 57:141–150, 1986; Loe et al., *J. Periodontol* 36:177–187, 1965; Suzuki, *Dent. Clin. North. Am.* 32:195–216, 1988). There are several types of gingivitis, the most common being chronic or long-standing plaque-induced gingivitis (Tanner et al., *Clinical Infectious Diseases* 16:304–309, 1993). A gummy film that coats the surface of the teeth, plaque results from the metabolic processes of normal mouth micro-organisms. These bacteria colonize the dental and tissue surfaces where they convert simple sugars into carbohydrates which accumulate to form plaque. If plaque is not removed within 24–36 hours after deposit, the bacteria produce toxins that cause inflamed and swollen gums. Other forms of gingivitis include acute necrotizing ulcerative gingivitis, as well as gingivitis resulting as a side effect of drug treatment such as diphenylhydontoin. As mentioned above, gingivitis can lead to periodontitis, which is characterized in a loss of alveolar support to the teeth, resulting in bone erosion and loose teeth. Periodontitis is the major cause of tooth loss in adults in the United States, and it is estimated that 50% of adults in the United States over the age of 45 are afflicted with periodontitis.

Plaque is known to play a role in the etiology of both gingivitis and periodontitis, and removing plaque is an effective treatment for the control of gingivitis (Dahlen et al., *J. Clinical Periodontology* 20:359–365, 1993). However, removal of plaque is generally performed under the supervision of a dentist or oral physician, which can be both expensive and inconvenient. Thus, a great detail of research has been directed to agents which can effectively remove plaque and/or treat periodontal disease, including the following: U.S. Pat. No. 4,963,346 to Amer is directed to the use of phytosterols (namely sitosterol, campersterol and stigmasterol) for the treatment or prevention of dental plaque, calculus and gingivitis; U.S. Pat. No. 3,914,406 to Yankell is directed to use of amine fluorides for preventing and treating gingivitis by administering the same to the oral cavity; U.S. Pat. No. 4,160,821 to Sipos is directed to the use of glycerin solution of zinc salt (especially zinc chloride) for the treatment of gingivitis; U.S. Pat. No. 5,281,410 to Lukacovic et al. is directed to the use of stannous compounds for reducing plaque and gingivitis; U.S. Pat. No. 5,326,554 to Fitz is directed to bicarbonate and carbonate compositions for treating plaque and gingivitis; U.S. Pat. No. 5,300,289 to Garlich et al. is directed to the use of phytic acid compositions for controlling dental calculus, dental plaque, gingivitis, periodontitis and oral maloder; and U.S. Pat. No. 5,298,237 to Fine is directed to gel compositions containing ascorbic acid and copper sulfate for the prevention or treatment of gingivitis, pariodontitis and plaque.

Although plaque is considered essential for the development of gingivitis and periodontitis, its presence, even in large amounts, does not necessarily lead to gingivitis, or to progression of gingivitis to the more severe periodontitis. This has led many investigators to postulate the involvement of other factors, including mental, physical and biological stress. Stress has been correlated to severity of periodontal disease in humans, associated with changes in bone in stressed laboratory animals, and changes in the cellular and fibrous components of the periodontium (Bartold et al., p. 1113). It is believed that stress-induced release of substance P from sensory nerve fibers in the oral mucosa, connective tissue of the dental pulp and the salivary gland is a causative agent of periodontal disease, particular the neurogenic inflammation characteristic of gingivitis and periodontitis. This has been further confirmed by studies which demonstrate that pretreatment of the oral mucosa with capsaicin, which is known to damage substance P immunoreactive nerves, prevents neurogenic inflammation upon local administration of substance P (Gyöfi et al., *J. Periodont. Res.* 28:191–196, 1993).

Administration of agents which modulate substance P would have significant utility over a wide range of disorders or conditions associated with substance P. For example, in addition to the prevention and/or treatment of periodontal disease, such agents would have utility in preventing and/or treating pain, neurogenic inflammation, headaches, migraine, neurological disorders, respiratory disorders, blood pressure, hematopoiesis, allergies, asthma, arthritis, irritable bowel syndrome, hemorrhoids, anal fissures, ulcerative colitis, Crohn's disease, proctitis, benign prostatic hypertrophy (BPH), cystitis, skin disorders, CNS disorders (such as Parkinson's disease, MS and Alzheimer's disease), as well as infertility, emesis, cough, bronchitis, osteoporosis, ulcers, fever and obesity. In this regard, it has been suggested that an ideal agent would have the ability to resist peptidases, and have the ability to enter the CNS (Lembeck, *Ann. N.Y. Acad. Sci.* 632:490–493, 1991).

Accordingly, there is a need in the art for agents which modulate substance P, as well as methods related to the use of such agents to prevent and/or treat conditions associated with substance P. There is also a need in the art for synthetic routes to make such agents. The present invention fulfills these needs, and provides further related advantages.

SUMMARY OF THE INVENTION

Briefly stated, the present invention discloses compounds which modulate substance P, and methods for the use thereof. In the context of this invention, such compounds contain calcium sulfate, and are hereinafter referred to as "calcium sulfate compounds." Preferred calcium sulfate compounds of this invention include, but are not limited to, syngenite, görgeyite and gypsum.

The calcium sulfate compounds of the present invention have utility as substance P modulating agents, as well as in the prevention and/or treatment of a wide variety of conditions associated with substance P. Thus, in one embodiment, a calcium sulfate compound of this invention is administered to a warm-blooded animal in need thereof to modulate substance P. In another embodiment, a calcium sulfate compound is administered to a warm-blooded animal in need thereof to prevent and/or treat a condition associated with substance P.

In a further embodiment of this invention, a calcium sulfate compound is administered to the oral cavity of a warm-blooded animal to prevent and/or inhibit periodontal disease, such as gingivitis and/or periodontitits.

In yet a further embodiment, a calcium sulfate compound is administered to a warm-blooded animal to prevent and/or treat pain, neurogenic inflammation, headaches, migraines, neurological disorders, respiratory disorders, blood pressure, hematopoiesis, allergies, asthma, arthritis, irritable bowel syndrome, hemorrhoids, anal fissures, ulcerative colitis, Crohn's disease, proctitis, benign prostatic hypertrophy, cystitis, skin disorders, and CNS disorders (such as Parkinson's disease, multiple sclerosis and Alzheimer's disease), as well as infertility, emesis, cough, bronchitis, osteoporosis, ulcers, fever and obesity.

In still a further embodiment, synthetic methods for the manufacture of syngenite and görgeyite are disclosed.

Other aspects of the present invention will become evident upon reference to the following drawings and detailed description. To this end, certain references are listed herein for purpose of illustration and reference, and are incorporated herein by reference in their entirety.

DETAILED DESCRIPTION OF THE INVENTION

Figure 1A:
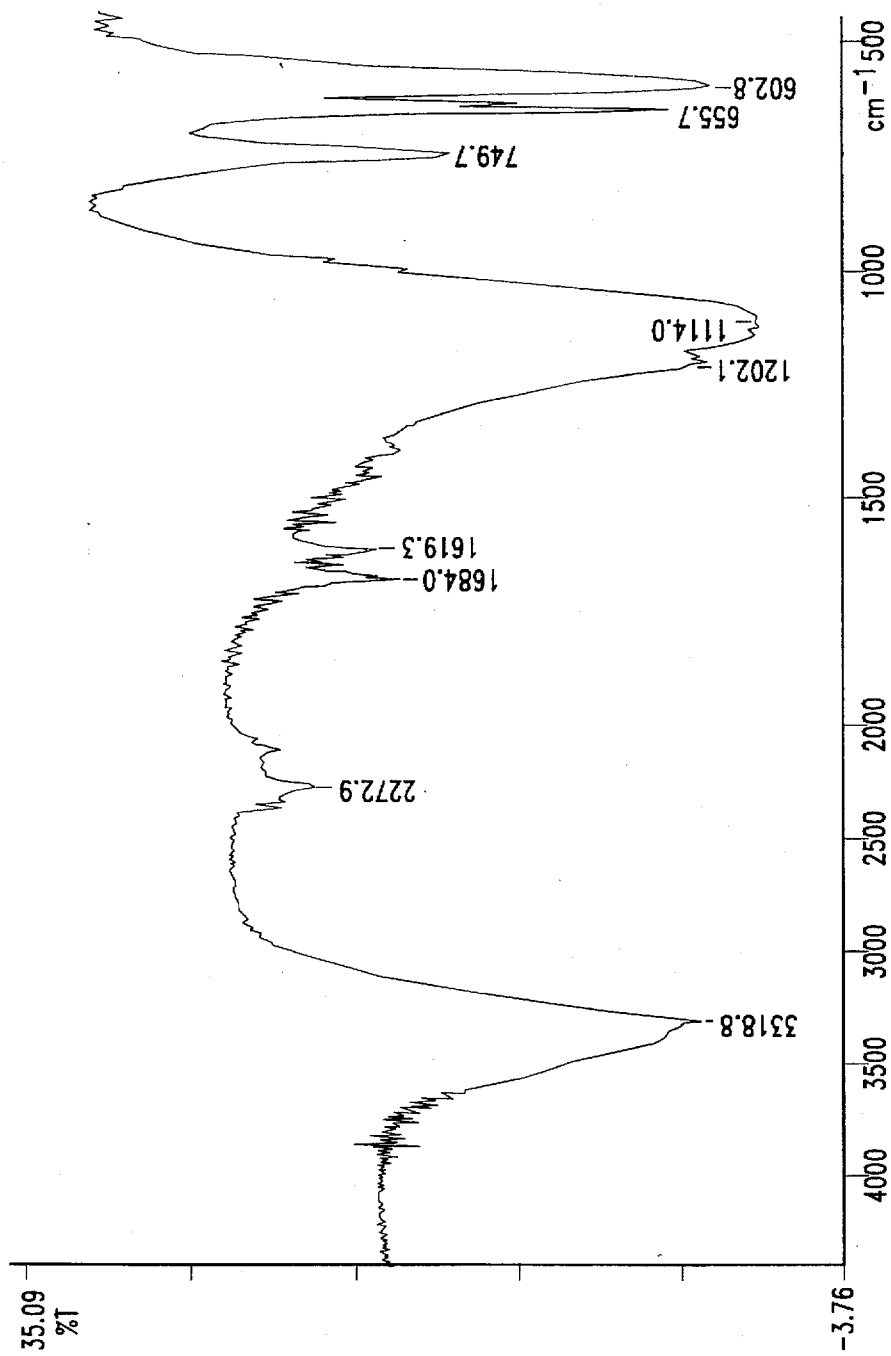
FIG. 1A is an IR spectrum.

As mentioned above, this invention is generally directed to compounds containing calcium sulfate (referred to herein as "calcium sulfate compounds"). Such calcium sulfate compounds modulate substance P, and therefor have utility as modulating agents of substance P, as well as in the prevention and/or treatment of a wide variety of conditions associated with substance P in warm-blooded animals, including humans.

As used herein, the term "conditions" includes diseases, injuries, disorders, indications and/or afflictions which are associated with substance P. Conditions "associated with substance P" are those conditions which result, either directly or indirectly, from release of substance P and/or abnormally high levels of substance P. The term "treat" or "treatment" means that the symptoms associated with one or more conditions associated with substance P are alleviated or reduced in severity or frequency, and the term "prevent"

means that subsequent occurrence of such symptoms are avoided or that the frequency between such occurrences is prolonged. The phrase "modulate substance P" means that substance P is regulated, adjusted, or adapted to a desired degree. For example, modulation of substance P may involve the prevention, inhibition or antagonization of substance P release, or that substance P, once released, is bound, complexed, impaired, scavenged or otherwise removed or affected as a causative agent of the condition.

A calcium sulfate compound of this invention contains, at a minimum, calcium sulfate ($CaSO_4$) as a component thereof. Calcium sulfate may be present in the compound in a non-hydrated or hydrated form (or mixture thereof). It should be understood that reference herein to "components" of the calcium sulfate compound include associated, disassociated, ionic, neutral, elemental, salt, hydrated and other forms or mixtures thereof. For example, calcium sulfate may be present within the compound in an associated form as a neutral or ionic species; as part of a larger complex; or in a disassociated form in which calcium and sulfate are present as distinct, non-complexed neutral or ionic species.

In one embodiment, the calcium sulfate compound is selected from calcium sulfate dihydrate or "gypsum" ($CaSO_4 \cdot 2H_2O$), calcium sulfate hemihydrate ($CaSO_4 \cdot \frac{1}{2}H_2O$) and anhydrous calcium sulfate ($CaSO_4$). Anhydrous calcium sulfate, as well as its hemihydrate and dihydrate forms, are commercially available from a variety of sources (e.g., J. T. Baker Inc., Phillipsburg, Pa.; Sigma Chemical Co, St. Louis, Mo.; Aldrich Chemical Co., Milwaukee, Wis.). For example, calcium sulfate dihydrate may be obtained from natural sources, such as gypsum rock, which may then be calcined to the hemihydrate or anhydrous form. The above forms of calcium sulfate may also be synthesized from various chemical processes, including production as a by-product of citric acid manufacturing techniques, with appropriate calcination or hydration to yield the desired form.

In another embodiment, calcium sulfate is complexed with one or more sulfate-containing components having a constituent selected from potassium, magnesium, aluminum, sodium, lithium, silicon, chlorine, cobalt, strontium, chromium, zinc, copper, iron, tin, nickel and manganese. Preferred sulfate-containing components include $K_2SO_4$, $MgSO_4$, $Al_2(SO_4)_3$, $Na_2SO_4$, $Li_2SO_4$, $Cr_2(SO_4)_3$, $MnSO_4$, $FeSO_4$, $Fe_2(SO_4)_3$, $CoSO_4$, $NiSO_4$, $CuSO_4$, $ZnSO_4$, $BaSO_4$, $SnSO_4$ and $SrSO_4$.

In a further embodiment, the sulfate-containing component is potassium sulfate ($K_2SO_4$), and the calcium sulfate compound is a calcium sulfate and potassium sulfate complex ($CaSO_4 \bullet K_2SO_4$). In a preferred embodiment, the calcium sulfate compound is syngenite ($CaSO_4 \bullet K_2SO_4 \bullet H_2O$) or görgeyite ($5CaSO_4 \bullet K_2SO_4 \bullet H_2O$). Syngenite and görgeyite are naturally occurring intermediate phases of potassium sulfate, calcium sulfate and water (i.e., $K_2SO_4$—$CaSO_4$—$H_2O$). Their crystal structure results from the regular repetition of nine-fold and eight-fold coordination polyhedra, and water is present in both minerals as discrete molecules. Syngenite occurs sparingly as a volcanic product and in salt deposits of oceanic origin. It is also found as crusts on lava in Heleakala crater (Maui, Hi.), as well as being present in natural deposits in Italy, Germany, Poland, Australia and China. Similarly, görgeyite occurs in Ischle salt deposits in Austria, in file Q Basin, Hubei Province, China (Mayrhofer, *Am. Min.* 39:403, 1954). Both syngenite and görgeyite have been described in a variety of mineralogical references (see *Encyclopedia of Minerals*, W. L. Roberts et al., Van Nostrand Reinhold Co., New York, N.Y., 1990; *Mineral Reference Manual*, E. H. Nickel and M. C. Nichols, Van Nostrand Reinhold Co., New York, N.Y., 1991; Paleche et al., *Dana's System of Mineralogy*, v.II, pp. 442–444, Wiley, N.Y., 1951).

Syngenite and görgeyite can be collected or synthesized by methods known to those skilled in this field. For example, syngenite and görgeyite can be collected from mineral deposits, and syngenite can be synthesized as disclosed in PCT Publication No. WO 94/09798. Synthetic routes for syngenite also include those disclosed in U.S. Pat. No. 4,554,139 to Worthington et al.; Calistru et al., Romanian Patent No. 88,488 (Chem. Abstracts 106:31984k, 1986); Yunusova et al., *Izu. Akad. Nauk Kirg. SSR, Khim-Tekhnol. Biol. Nauki* 1:13–15, 1990 (Chem. Abstracts 114:84755h, 1990); and PCT Publication No. WO 94/09798. Synthetic techniques for görgeyite have similarly been reported (Krull et al., *Z. Krist.* 86:389–394, 1933).

In one embodiment of this invention, synthetic routes for the manufacture of syngenite and görgeyite are disclosed. In this regard, highly pure syngenite can be manufactured in high yield by mixing potassium chloride and potassium sulfate with calcium chloride. More specifically, potassium chloride and potassium sulfate are dissolved in water at a molar ratio of potassium sulfate to potassium chloride ranging from 10:1 to 1:25, and preferably 1:1 to 1:6. This can be achieved at a temperature ranging from 20°–80° C., and preferably from 25°–45° C., with constant stirring. Calcium chloride is then added, preferably pre-dissolved in water, to the stirring potassium chloride/potassium sulfate solution to yield a molar ratio of calcium chloride to potassium sulfate ranging from 10:1 to 1:25 (preferably ranging from 1:1 to 1:8), and a molar ratio of calcium chloride to potassium chloride ranging from 10:1 to 1:25 (preferably ranging from 1:1 to 1:9). The resulting solution yields syngenite as vitreous white precipitate. The precipitate may then be filtered and washed with either a combination of ethanol/water (1:4) solution and then with water, or simply washed with water (preferably cold) to yield syngenite in excess of 90% purity.

In a preferred embodiment potassium sulfate and potassium chloride are dissolved in water at a molar ratio ranging from 3:1 to 1:3 with constant stirring, and at a temperature ranging from 20°–80° C. (preferably 25°–45° C.). Calcium chloride is then added, preferably pre-dissolved in water, to the above stirring solution at a calcium chloride to potassium sulfate molar ratio ranging from 3: 1 to 1:3 with constant stirring at a temperature ranging from 20°–80° C. (preferably ranging from 25°–45° C.). To this solution, additional potassium chloride is then added. The molar ratio of the previously added potassium chloride to the additional potassium chloride ranges from 3:1 to 1:3. The resulting solution yields syngenite as vitreous white precipitate. The precipitate may then be filtered and washed with water (preferably cold) to yield syngenite at a purity in excess of 90%.

In a further synthetic technique, a relatively fast and efficient method for the synthesis of görgeyite is disclosed. In this technique, a calcium sulfate-containing compound and potassium sulfate are dissolved in water at a molar ratio ranging from 7:1 to 1:70, and preferably ranging from 1:1 to 1:20. The resulting solution is then heated to a temperature at or near its boiling point and ranging from 80°–100° C. (preferably 90°–100° C.), and preferably under reflux, for a period of time ranging from 2 to 10 hours, preferably from 6 to 8 hours. In this synthetic technique, the calcium sulfate-containing compound may be calcium sulfate dihydrate, calcium sulfate hemihydrate or anhydrous calcium suflate, or may be syngenite. Upon cooling, görgeyite forms as a precipitate which may be removed from the solution by filtration. The precipitate may then be washed either with a combination of ethanol/water (1:5) solution and then with water, or simply washed with water (preferably cold) to yield görgeyite in excess of 90% purity.

While the calcium sulfate compounds of the present invention have been disclosed individually above, it should be understood that this invention encompasses compositions of two or more calcium sulfate compounds, as well as compositions containing at least one calcium sulfate compound in combination with other organic and/or inorganic constituents and/or other active constituents.

The calcium sulfate compounds of this invention have been found to modulate substance P, and are relatively stable due to their resistance to degradation by, for example, peptidases. As mentioned above, substance P is an undecapeptide and a member of the tachykinin class of neuropeptides. Substance P is found in secretory granules of sensory neurons which are designated as substance P immunoreactive ("SP-IR") nerves. The primary function of the SP-IR nerves are for nociceptive information which, upon stimulation by noxious stimuli, release substance P and thereby mediate pain perception. However, release of substance P and other neuropeptides from collateral nerve terminals and peripheral tissues result in neurogenic inflammation. Thus, the calcium sulfate compounds of this invention can be used to inhibit neurogenic inflammation by modulating substance P.

In addition, the calcium sulfate compounds of this invention may be used to prevent and/or treat a variety of conditions associated with substance P. SP-IR nerves, and thus substance P itself, are found in many different tissues, including the central and peripheral nervous system, smooth muscles of the arteries and veins, pulmonary, urinary and gastrointestinal tracts, basal ganglia, substantia nigra, striatonigral pathways, hypothalamus, retina, gingival tissue, prostate gland and even in spermatozoa. Due to its nearly ubiquitous distribution in mammalian tissue, substance P is believed to be associated with a variety of conditions. In addition to its involvement in pain mediation and promotion of neurogenic inflammation, substance P is associated with periodontal disease, headaches and migraines, emesis, vomiting and nausea, cough (of both vital and bacterial origin), chronic bronchitis, immune system stimulation and regulation, hematopoieses, neurological disorders, respiratory disorders, allergies, fertility, female reproductive cycle control and regulation of spermatogenesis in males, obesity, osteoporosis/bone regulation, spasmodic conditions, ulcers, blood pressure regulation, stress response conditions, irritable bowel syndrome, hemorrhoids, anal fissures, and BPH/prostate conditions.

Accordingly, the calcium sulfate compounds of this invention are believed effective in preventing and/or treating the above conditions due to their ability to modulate substance P. To this end, the calcium sulfate compounds of the present invention may be utilized for pharmaceutical, prophylactic and/or cosmetic purposes, and are administered to a warm-blooded animal in an effective amount to achieve a desired result. In the case of pharmaceutical administration, an effective amount is a quantity sufficient to treat the symptoms of a condition and/or the underlying condition itself. An effective amount in the context of prophylactic administration means an amount sufficient to avoid or delay the onset of a condition and/or its symptoms. Lastly, an effective amount with regard to cosmetic administration is an amount sufficient to achieve the desired cosmetic result.

In a preferred embodiment, the calcium sulfate compounds of the present invention are administered to a warm-blooded animal as a pharmaceutical, prophylactic or cosmetic composition containing at least one calcium sulfate compound in combination with at least one pharmaceutically, prophylactically or cosmetically acceptable carrier or diluent. Such compositions typically contain a calcium sulfate compound or compounds in an amount ranging from 0.01% to 85%, typically from about 0.05% to 50% and preferably from about 0.1% to 20% by weight of the composition. Administration may be accomplished by systemic or topical application, with the preferred mode dependent upon the type and location of the conditions to be treated. Frequency of administration may vary, and is typically accomplished by daily administration.

Systemic administration may be achieved, for example, by injection (e.g., intramuscular, intravenous, subcutaneous or intradermal) or oral delivery of the composition to the warm-blooded animal. Suitable carriers and diluents for injection are known to those skilled in the art, and generally are in the form of an aqueous solutions containing appropriate buffers and preservatives. Oral delivery is generally accomplished by formulating the composition in a liquid or solid form, such as a tablet or capsule, by known formulation techniques.

Topical administration may be accomplished, for example, by formulating the composition as solution, cream, gel, ointment, powder, paste, gum or lozenge using techniques known to those skilled in the formulation field. As used herein, topical administration includes delivery of the composition to mucosal tissue of the mouth, nose and throat by, for example, spray or mist application, as well as to the vagina and rectum by, for example, suppository application.

In one embodiment of this invention, a composition containing one or more calcium sulfate compounds is formulated for topical administration to the oral cavity of a warm-blooded animal. In this embodiment, the composition is administered topically to the oral cavity, held therein for a period of time, and then largely expectorated (rather than swallowed). Such compositions include toothpastes, tooth gels, tooth powders, mouthwashes, mouth sprays, propylaxyis pastes, dental treatment solutions, oral gels, lozenges, chewing gums, controlled-releases drug delivery systems for placement in the periodontal pocket, and the like. Components of topical, oral compositions are those that are generally suitable for administration to the oral cavity, and are compatible with the calcium sulfate compounds of this invention. In this context, "compatible" means that the components of the composition are capable of being commingled with one another, in a manner such that there is no interaction which would substantially reduce the efficacy of the composition under normal use. Such components are well known in the art, and include (but are not limited to) anticarries agents, antiplaque agents, anticalculas agents, dental abrasives, surfactants, flavoring agents, sweetening agents, binders, humectants, thickening agents, buffering agents, preservatives, coloring agents, pigments, alcohol (e.g., ethanol) and water.

A composition of this invention may be administered to an animal in need thereof to modulate substance P. In one embodiment, the composition is administered to the oral cavity for the prevention and/or treatment of a periodontal disease, such as gingivitis or periodontitits. This may be accomplished by contacting the soft tissue afflicted with gingivitis or periodontitis for about 15 seconds, preferably from about 20 seconds to 10 minutes, and more preferably from about 30 seconds to 1 minute. The composition may then be expectorated from the oral cavity. The frequency of such administration is preferably from about once per week to about four times per day, and more preferably once or twice per day.

The compositions of the present invention are believed to function with regard to the prevention and/or treatment of periodontal disease by modulating substance P and by controlling the temperature of gingival tissues. Temperature as a periodontal diagnostic tool has recently been reported (Kung et al., *J. Clin. Periodontology* 7:557–563, 1990; Isogai et al., *J. Periodontology* 65:710–712, 1994). It is believed that release of substance P within the tissues of the oral cavity increases the temperature of gingival tissues. Such a temperature elevation provides a more favorable environment for microbial growth, which results in the onset or worsening of gingivitis and/or periodontitis (see Hoffajee et al, *J. Clin. Periodontology* 19:417–422, 1992). Administration of the compositions of this invention to the oral cavity results in substance P modulation and a lowering of gingival tissue temperature which, in turn, leads to less favorable conditions for bacterial growth.

While others have suggested using calcium sulfate hemihydrate for treating periodontal disease (see Published PCT WO 91/11168 to Robinson), preventing periodontal disease by administering calcium sulfate hemihydrate has not been reported, nor would it be expected absent recognition that the calcium sulfate compounds of this invention function as substance P modulating agents. To this end, others have suggested use of syngenite to prevent or treat a variety of conditions, such as wound healing, pain and inflammation (see Published PCT No. 94/09798 to Hart et al.). However, such disclosure does not recognize activity of the calcium sulfate compounds of this invention as agents which modulate substance P. It has now been discovered that the calcium sulfate compounds of this invention have the ability to modulate substance P, and thus have utility in the prevention and/or treatment of a wide range of conditions associated with substance P.

The ability of the calcium sulfate compounds of this invention to modulate substance P may be assayed by known techniques, such as those disclosed by Mizrahi et al. (*Eur. J. Pharmacol.* 91:139–140, 1983) and Holzer et al. (*P. Eur. J. Pharmacol.* 91:83–88, 1983). For example, PanLabs Test Numbers 3-0580 screen the ability of compounds to function as substance P antagonists by determining the ability of the compound to inhibit substance P-induced contractions of guinea pig ileum (see Example 6 herein below).

Substance P plays a role in the release of various immunomodulatory cytokines produced by macrophages, such as tumor necrosis factor (TNF) and interleukin 1 (IL-1). Such cytokines induce release of prostaglandin $E_2$ ($PGE_2$) which plays a major role in the pathogenesis of bone and cartilage destruction in inflammatory diseases. Utility of the calcium sulfate compounds of this invention as immunomodulatory agents may be assayed by a number of commercially available techniques, including the techniques disclosed by Maloff et al. (*Clin. Chim. Acta.* 181:73–78, 1989). Representative assays include, for example, PanLabs Test Numbers 4-0140 and 4-0120 which screen agents for the ability to inhibit (or promote) $PGE_2$ release from cells exposed to TNF and IL-1, respectively.

Similarly, the ability of the calcium sulfate compounds of this invention to bind to the neurokinin $NK_1$ receptor may be determined by the procedure of Lee et al. (*Mol. Pharmacol.* 23:563–569, 1983). In this assay, submaxillary glands are obtained from male guinea pigs and a membrane fraction prepared by standard techniques. The membrane preparation is then incubated with labeled substance P, and non-specific binding is estimated in the presence of the test compound. The membranes are then filtered and washed, and the filters are counted to determine bound, labeled substance P.

Fever is a defense mechanism which is regulated in the central nervous system and, more specifically, in the preoptic area of the anterior hypothalamus. This area has been known to play an important regulatory role in body temperature (Blatteis et al., *Ann. of NY Acad. Sci.* 741:162–173, 1994). It is also known that substance P containing nerve cell terminals are present in the preoptic area of the anterior hypothalamus (Gallagher, *Brain Research Bull.* 20:199–207, 1992). In a guinea pig model of fever, IV injection of an exogenous pyrogen increased colonic temperature as measured using thermocouples. Substance P antagonist microinjected intrapreoptically attenuated the fevers showing that substance P inhibition results in reduced febrile response. In addition, when substance P was microinjected into the preoptic area of conscious guinea pigs, it caused an increase in temperature, whereas a substance P antagonist significantly attenuated the febrile response to IV pyrogen stimulation. Thus, the calcium sulfate compounds of this invention have activity in decreasing the febrile response in mammals.

It is postulated that release of sensory neuropeptides including substance P, neurokinin A and calcitonin-gene-related peptide may be one of the mechanisms of migraine pathogenesis (Buzzi et al., *Br. J. Pharmacology* 99:202–206, 1990). Moussaoiu et al. (European Journal of Pharmacology 238:421–424, 1993) suggest that selective NK1 receptor antagonists could be greatly effective in humans for the treatment of migraine headaches. Capsaicin, a substance P inhibitor, was reported to decrease the severity of cluster headaches when administered intranasally to humans (Marks et al., *Cephalalgia* 13:114–116, 1993). Thus, the calcium sulfate compounds of this invention are useful in the treatment of migraine headaches, particularly via intranasal administration.

Impaired thermogenesis is thought to be the primary reason for obesity, although other mechanisms also play a role (Williams et al., *Clinical Sci.* 80:419–426, 1991). The hypothalamus is an important organ for control of food intake and thermogenesis. It contains over 50 putative neurotransmitters, among these substance P (Morely, *Endocrine Rev.* 8:257–287, 1987). High concentrations of substance P have been found in the ventro-medial hypothalamus which is the satiety center in mammalian species (Iverson, *Br. Med. Bull.* 38:277–282, 1982). Baroncenelli et al. (*Functional Neurology* 4:183–184, 1989) reported that plasma concentrations of substance P in obese children were significantly higher as compared to controls. They found a positive correlation between substance P levels and percentage of weight gain. Thus, the calcium sulfate compounds of this invention may be used as weight loss agents modifying plasma substance P levels.

It is known that the mammalian stomach is widely innervated by capsaicin-sensitive afferent neurons (Shatkey et al., *Gastroenterology* 87:914–921, 1984). Substance P inhibitors, such as capsaicin, when given intragastrically prior to challenge with 30% ETOH, reduced the area of stomach injury. Substance P, when given IV, increased the areas of injury (Katori et al., *Regulatory Peptides* 46:241–243, 1993). It was further noted in the ulcerogenic rat model that the level of substance P in gastric fluid was increased significantly after challenge with 50% ETOH. In such a model of ulcerogenesis, the calcium sulfate compounds of this invention offer protection to the gastric mucosa, and thus may be used as a treatment for ulcers.

Vomiting and nausea occur in a wide variety of disorders such as peptic ulcer disease, peritonitis, acute systemic infections with fever, elevated intracranial pressure, morning sickness of early pregnancy, myocardial infarction and as a side effect of many drugs, ingested chemicals and anesthesia. Patients undergoing chemotherapy and radiation therapy for cancer also experience vomiting as a side effect. The nucleus tractus solitarius is the region in the brain where gastric vagal afferent fibers terminate, and this area is innervated by substance P-containing fibers (Otuska, *Physiology Review* 73:229, 1993). It has been suggested that substance P which is released by cytotoxic agents may induce emesis. It is also known that substance P is an emetic (Andrews et al., *Trends Pharmacol. Sci.* 9:334, 1988). Consequently, the calcium sulfate compounds of this invention are expected to attenuate emesis. In this context, the ferret model of induced emesis is commonly used to test antiemetic drugs (Tattersall, *European J. of Pharmacol.* 250:R5–R6, 1993; Knox et al., *Brain Research Bull.* 31:477–484, 1993).

Substance P is a neuropeptide known to cause coughing (Kohrogi, *Journal of Clinical Investigation* 82:2063–2068, 1988). In particular, substance P is known to activate the cough reflex and capsaicin has been used as a provocative agent to test the sensitivity of the cough reflex (Morice et al., *Lancet ii*:1116–1118, 1987). Karlsson (*Thorax* 48:396–400, 1993) suggests that there is a role for substance P sensitive nerves in chronic, non-productive cough and sneezing. Yoshihara et al. (*Regulatory Peptides* 46:238–240, 1993) have reported that plasma substance P levels were higher in a pertussis group during the coughing stage than during the recovery stage or in the control group. In addition, it was also noted that the plasma substance P level decreased simultaneously with a decreasing number of coughing attacks. Thus, the calcium sulfate compounds of this invention may be used in the prevention and/or treatment of coughs of various etiologies.

Substance P immune reactive fibers have been localized in the anterior pituitary in the rat (Battmann et al., *J. Endocrinol.* 130:160–175, 1991) and in humans (Wormald et al, *J. Clin. Endocrinol. Matab.* 69:612–615, 1989). Substance Preceptors are present in ovaries (Wuttke, *Human Reproduction* 8(Suppl. 2):141–146, 1993) and in mouse and human testes (Chiwakta et al., *Endocrinology* 128:2441–2448, 1991). It has been reported that substance P may also be involved in the regulation of midcycle LH surges, and may be an important peptide in the regulation of reproductive events. It is also known that substance P is present in lactotrophs and gonadotropes in the rat anterior pituitary (Morel et al., *Neuroendocrinology* 35:86–92, 1982). The presence of substance P in these organs is apparently essential for reproduction. In addition, substance P may also play a role in the midcycle LH surge. Thus, the calcium sulfate compounds of this invention may be used to treat conditions of mammalian infertility.

Substance P neurons are found in afferent sensory branches of the trigeminal nerve which innervates the walls of the submucosal glands and blood vessels and the epithelium of the human nasal mucosa (Lundberg, *Am. Rev. Respir. Dis.* 137):S16–S23, 1987). Chaen et al. (*Ann. Otol. Rhinol. Laryngol.* 102:16–21, 1993) reported that substance P is actively secreted into the nose and may play an important role in nasal mucosa allergy reactions. Substance P is also reported to act as a mast cell secretagogue (Repke et al., *FEBS Letters* 221(2):236–240, 1987). It is known that substance P induces mucosecretion in human bronchi (Rogers et al., *European J. of Pharmacol.* 74:283–286, 1989). Braunstein et al. (*Am. Rev. Respir. Dis.* 144:630–635, 1991) reported that exogenously applied substance P causes an increase in nasal protein output in allergic rhinitis patients, and that substance P may play a role in allergic thiniris. Thus, the calcium sulfate compounds of this invention may be used to treat allergic reactions such as allergic rhinitis, as well as other conditions in which there is nasal obstruction and/or abnormal mucus secretions, such as the common cold and acute and chronic bronchitis.

The following examples are offered by way of illustration, and not by way of limitation.

EXAMPLES

The following examples present the preparation, characteristics and use of exemplary embodiments of the present invention. To summarize the examples that follow, Example 1 illustrates the synthesis of syngenite and görgeyite by various techniques; Example 2 illustrates the preparation and use of a mouth rinse containing syngenite or görgeyite; and Examples 3–4 illustrate use of the mouth rinse of Example 2 to treat periodontal disease; Example 5 illustrates use of a mouth rinse containing gypsum to prevent periodontal disease; Example 6 illustrates modulation of substance P by syngenite, görgeyite and gypsum; and Example 7 illustrates the non-toxic nature of syngenite.

Source of Chemicals

Chemicals utilized in the following examples may be purchased from a number of suppliers, including Sigma Chemical Co., St. Louis, Mo.; Aldrich Chemical Co., Milwaukee, Wis.; and J. T. Baker, Inc., Phillipsburg, Pa.

EXAMPLE 1

Synthesis of Syngenite and Görgeyite

A. Synthesis of Syngenite

Syngenite can be synthesized by mixing potassium chloride and potassium sulfate with calcium chloride.

Figure 1B:
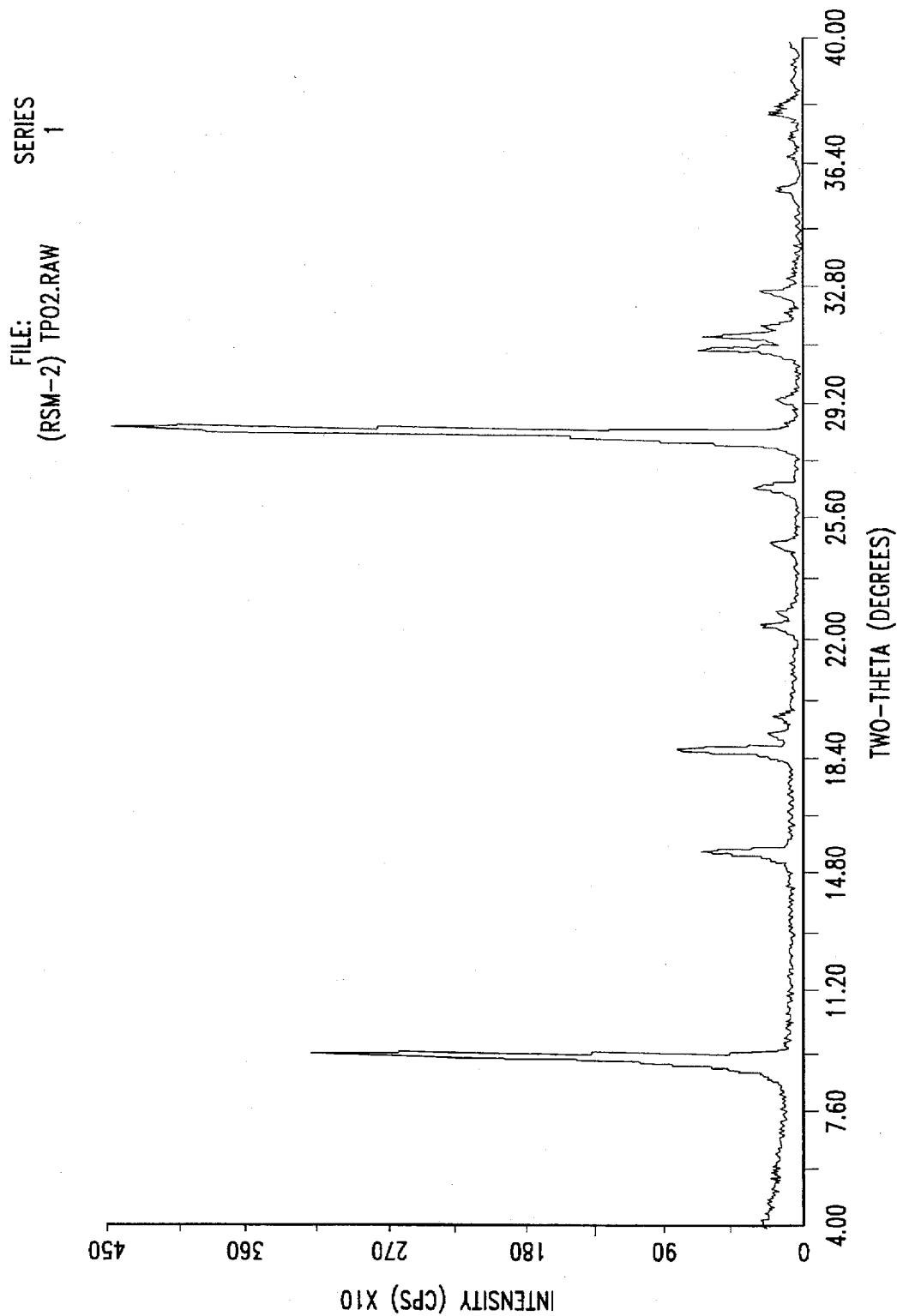
FIG. 1B presents an X-ray powder diffraction analysis, of syngenite made according to this invention.

In this example, calcium chloride dihydrate (0.136 moles) was dissolved in 100 ml water to yield a first solution. A second solution was prepared by completely dissolving potassium chloride (0.134 moles) and potassium sulfate (0,287 moles) in 900 ml water at 35° C. with constant stirring. The first solution was then added to the second solution and the resulting mixture stirred for 1 hour at 35° C. Potassium chloride (0.268 moles) was added to the mixture and stirred for additional 3 hours at 35° C. A vitreous white precipitate formed which was separated by filtration, and then washed with a small amount of cold water and dried to yield 0.106 moles of pure syngenite at a purity in excess of 90%. FIG. 1A is an infra-red (IR) spectrum of syngenite prepared by this method, while FIG. 1B represents X-ray powder diffraction analysis of the same.

B. Synthesis of Görgeyite

Figure 2A:
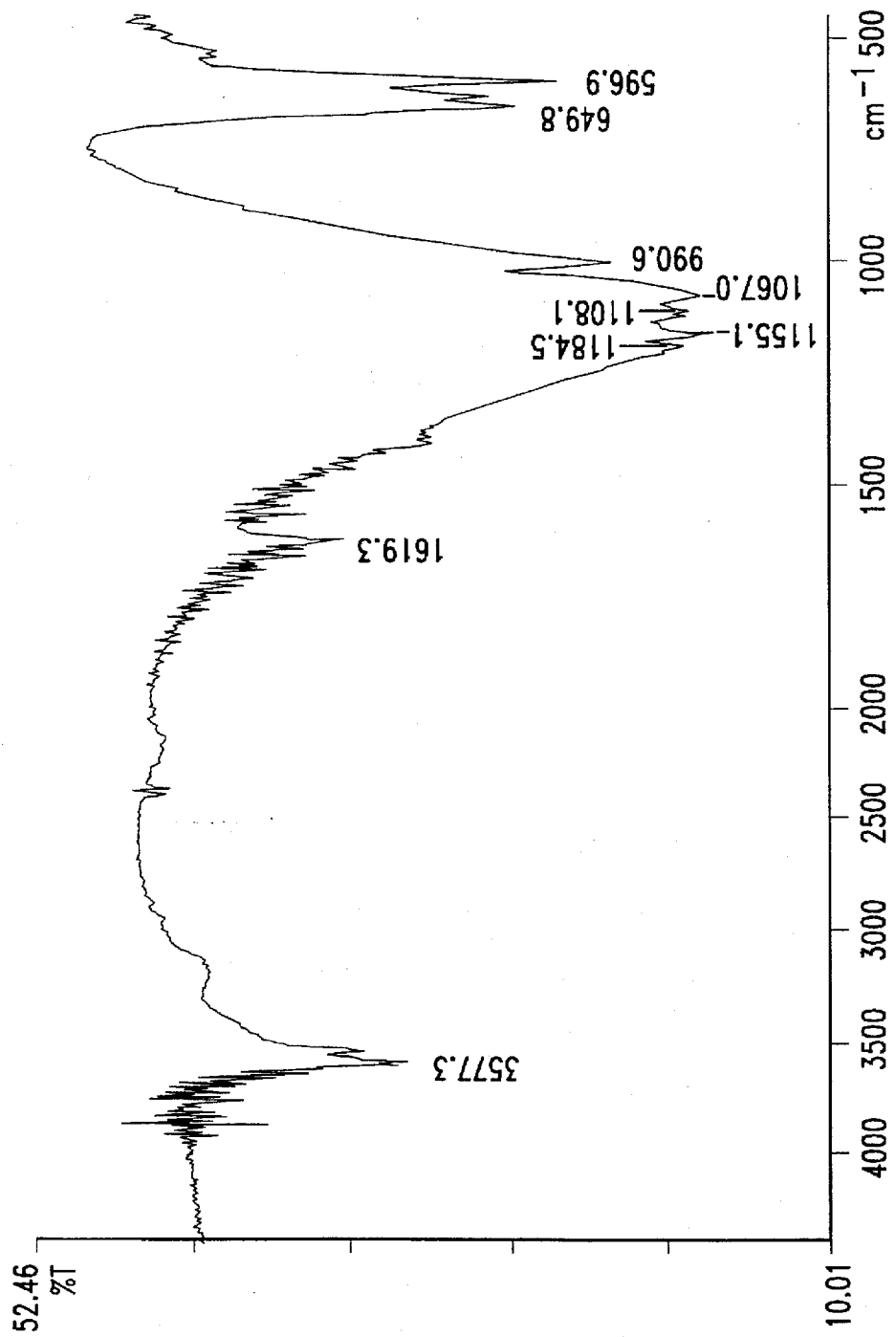
FIG. 2A is an IR spectrum.
Figure 2B:
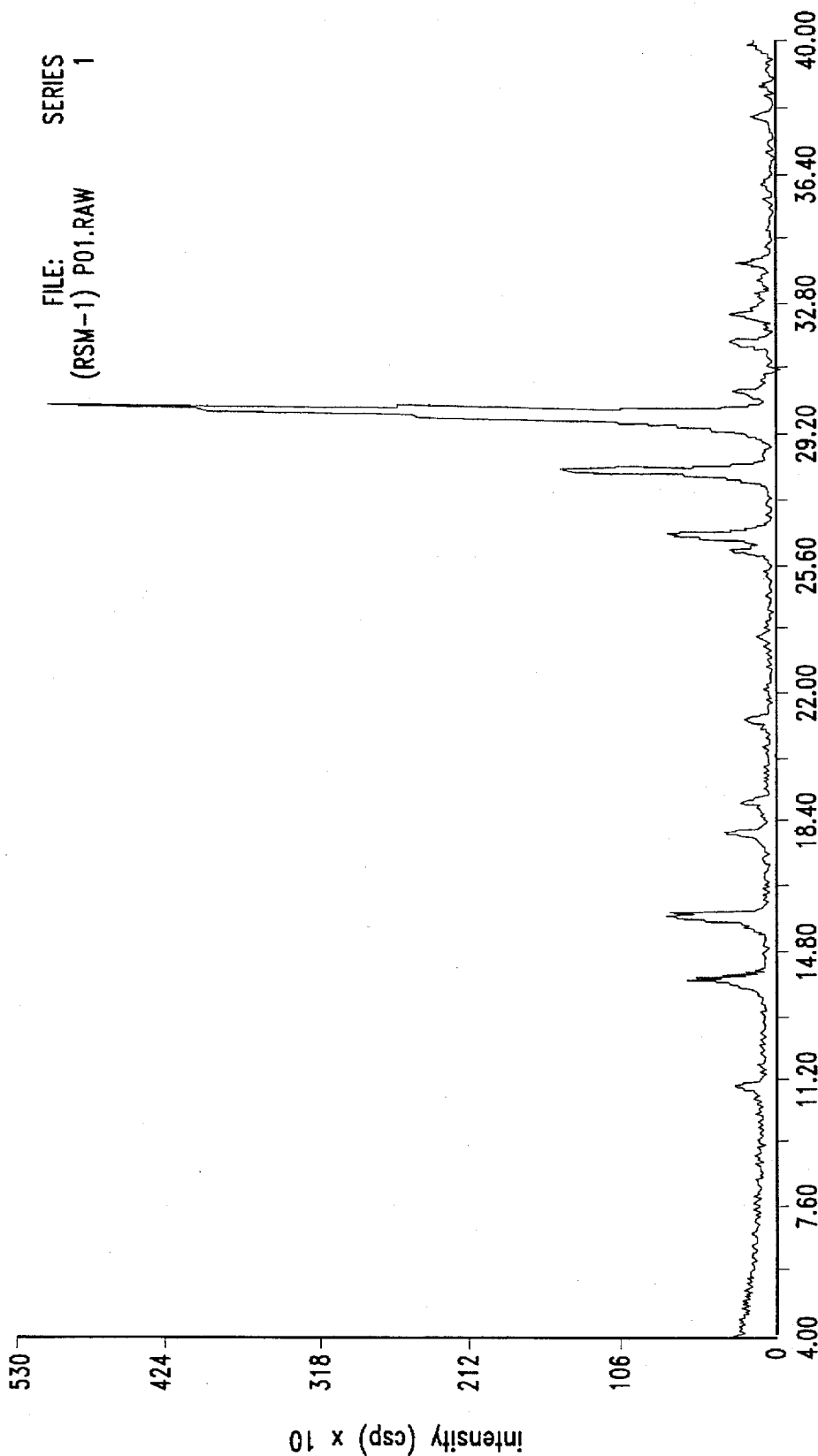
FIG. 2B presents an X-ray powder diffraction analysis, of görgeyite made according to this invention.

Potassium sulfate (71.84 mmoles) was completely dissolved in 250 ml water. To this solution was added calcium sulfate dihydrate (10.4 mmoles), which was then boiled under reflux for 8 hours. The resulting solution was filtered and the precipitate washed with cold water and then dried, yielding 1.54 mmoles of görgeyite at a purity in excess of 90%. FIG. 2A is an IR spectrum of görgeyite prepared by this method, while FIG. 1B presents an X-ray powder diffraction analysis of the same.

EXAMPLE 2

Preparation and Use of Mouth Rinse

A mouth rinse was prepared by mixing 0.3% w/v syngenite or görgeyite (as prepared by the procedures of Examples 1A and 1B, respectively) in drinking water. The mouth rinse was used without further modification in Examples 3 and 4. Patients were instructed to use the mouth rinse twice (2×) per day after brushing their teeth (i.e., morning and evening). After brushing, the patients placed approximately 10 ml of mouth rinse in their mouth and "swished" for 1–2 minutes, and then expectorated the solution from their mouth. The patients were further instructed not to immediately rinse their mouth with water after swishing.

EXAMPLE 3

Treatment of Periodontal Disease with Syngenite

In the following case studies, the administration procedures set forth in Example 2 were followed by the patients.

A. Case Study 1

A male patient in his early forties had a recent history of mild gingival inflammation and bleeding. The patient used the mouth rinse of Example 2 containing syngenite. After a few days of treatment, the bleeding was remarkably reduced and, after one week of treatment, gingival symptoms were completely gone. Treatment was then discontinued and the gingival symptoms have not recurred for five months post-treatment.

B. Case Study 2

A female patient in her fifties had a history of severe periodontal disease with gingival swelling, redness, bleeding, and loose and sensitive teeth. The patient used the mouth rinse of Example 2 containing syngenite for three months. After the first month of treatment, the gingival swelling, redness, sensitivity and bleeding were reduced. At the end of the second and third months of treatment, bleeding had ceased, and sensitivity was less than experienced at the end of the first month of treatment.

C. Case Study 3

A male patient in his mid-seventies had a history (over the past five years) of gingival bleeding and sensitive teeth. The patient began using the mouth rinse of Example 2 containing syngenite. After one week of treatment the patient experienced less bleeding of the gums and, after one month, bleeding had nearly ceased and his teeth were less sensitive. At the end of two months of treatment, bleeding of the gums ceased entirely.

EXAMPLE 4

Treatment of Periodontal Disease with Görgeyite

A male patient in his fifties has a history of severe periodontal disease. The patent begins use of a mouth rinse containing görgeyite as set forth in Example 2. After one month of treatment, the symptoms associated with the periodontal disease, such as gum bleeding, has significantly reduced.

EXAMPLE 5

Preventing Periodontal Disease with Gypsum

A male patient in his fifties has a past history of reoccurring periodontal disease. A mouth rinse containing 0.2% w/v gypsum is used by the patient according to the procedures set forth in Example 2. Reoccurrence of periodontal disease, and the symptoms associated therewith, do not reoccur after four months of use.

EXAMPLE 6

Modulation of Substance P by Syngenite, Görgeyite and Gypsum

This example illustrates the ability of representative calcium sulfate compounds of this invention to modulate substance P by functioning as substance P antagonists. Activity was measured by the procedures disclosed by Mizrahi et al. (Eur. J. Pharmacol. 91:139–140, 1983) and Holzer et al., (Eur. J. Pharmacol. 91:83–88, 1983). Specifically, isolated guinea pig ileum, bathed in physiological salt solution containing atropine (4.5 µM), diphenhydramaine (3.4 µM), and indomethacin (2.8 µM) at 37° C. was used. The ability of a test compounds to inhibit substance P-induced contractions of the illeum indicates antagonist activity. The results of this experiment are presented in Table 1.

TABLE 1

| Antagonism of Substance P | | |
|---|---|---|
| Compound | Concentration (µM) | Antogonist Activity (% Inhibition) |
| Syngenite | 100 | 40 |
| Görgeyite | 100 | 16 |
| Gypsum | 100 | 39 |

These results indicate that syngenite, görgeyite and gypsum are effective modulating agents of substance P.

EXAMPLE 7

Non-Toxicity Of Syngenite

This example illustrates the non-toxic nature of a representative calcium sulfate compound of this invention (i.e., syngenite).

To determine the potential toxicity and/or toxic effects of syngenite when administered as a single oral dose in rats, 5 male and 5 female Sprague Dawley rats (200–300 grams) were administered syngenite at a dose level of 5 g/kg body weight by syringe and suitable intubation tubes.

The body weight of each rat was recorded (in grams) just prior to administration of syngenite (Day 0), and weekly thereafter for two weeks (i.e., Day 7 and Day 14). This data are presented in Table 2.

TABLE 2

| Body Weight of Test Animals | | | | | |
|---|---|---|---|---|---|
| Rat | Sex | Day 0 | Day 7 | Day 14 | Change |
| 1 | F | 222 | 255 | 256 | +34 |
| 2 | F | 223 | 266 | 273 | +50 |
| 3 | F | 223 | 251 | 287 | +64 |
| 4 | F | 228 | 269 | 299 | +71 |
| 5 | F | 221 | 279 | 273 | +52 |
| 6 | M | 260 | 350 | 395 | +135 |
| 7 | M | 247 | 333 | 374 | +127 |
| 8 | M | 261 | 329 | 375 | +114 |
| 9 | M | 260 | 336 | 368 | +108 |
| 10 | M | 248 | 337 | 386 | +138 |

All test animals were observed for signs of toxicity and mortality twice daily for 14 days following administration.

All ten test animals survived the 14 day observation period. No clinical observations were noted during this period, and all animals appeared normal. No gross abnormalities in any of the animals were observed at necropsy.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for inhibiting substance P in a warm-blooded animal, comprising administering to an animal in need thereof an effective amount of görgeyite.

2. The method of claim 1 wherein the görgeyite is administered within a composition further comprising at least one pharmaceutically acceptable carrier or diluent.

3. The method of claim 2 wherein the görgeyite is present in the composition in an amount ranging from 0.05% to 50% by weight of the composition.

4. The method of claim 2 wherein the görgeyite is present in the composition in an amount ranging from 0.1% to 20% by weight of the composition.

5. The method of claim 2 wherein the composition is administered topically.

6. The method of claim 2 wherein the composition is administered systemically.

7. The method of claim 2 wherein the composition is administered orally.

8. The method of claim 2 wherein the composition is administered intranasally.

9. A method for reducing abnormally high levels of substance P in a warm-blooded animal, comprising administering to an animal in need thereof an effective amount of syngenite.

10. The method of claim 9 wherein the syngenite is administered within a composition further comprising at least one pharmaceutically acceptable carrier or diluent.

11. The method of claim 10 wherein the syngenite is present in the composition in an mount ranging from 0.05% to 50% by weight of the composition.

12. The method of claim 10 wherein the syngenite is present in the composition in an amount ranging from 0.1% to 20% by weight of the composition.

13. The method of claim 10 wherein the composition is administered topically.

14. The method of claim 10 wherein the composition is administered systemically.

15. The method of claim 10 wherein the composition is administered orally.

16. The method of claim 10 wherein the composition is administered intranasally.

* * * * *